United States Patent
Nam et al.

(10) Patent No.: US 11,539,025 B2
(45) Date of Patent: Dec. 27, 2022

(54) COMPOSITION FOR ORGANIC LIGHT EMITTING DIODE ENCAPSULATION AND ORGANIC LIGHT EMITTING DIODE DISPLAY MANUFACTURED THEREFROM

(71) Applicant: SAMSUNG SDI CO., LTD., Yongin-si (KR)

(72) Inventors: Seong Ryong Nam, Suwon-si (KR); Mi Jeong Choi, Suwon-si (KR); Sung Min Ko, Suwon-si (KR); Bum Jin Lee, Suwon-si (KR)

(73) Assignee: Samsung SDI Co., Ltd., Yongin-si (KR)

( * ) Notice: Subject to any disclaimer, the term of this patent is extended or adjusted under 35 U.S.C. 154(b) by 249 days.

(21) Appl. No.: 16/632,818

(22) PCT Filed: Jul. 5, 2018

(86) PCT No.: PCT/KR2018/007657
§ 371 (c)(1),
(2) Date: Jan. 21, 2020

(87) PCT Pub. No.: WO2019/017630
PCT Pub. Date: Jan. 24, 2019

(65) Prior Publication Data
US 2021/0151713 A1 May 20, 2021

(30) Foreign Application Priority Data

Jul. 21, 2017 (KR) .......................... 10-2017-0093003

(51) Int. Cl.
| | |
|---|---|
| *C07D 209/24* | (2006.01) |
| *H01L 51/52* | (2006.01) |
| *C07F 7/08* | (2006.01) |
| *C08F 122/14* | (2006.01) |
| *H01L 51/00* | (2006.01) |

(52) U.S. Cl.
CPC ........ *H01L 51/5253* (2013.01); *C07D 209/24* (2013.01); *C07F 7/0838* (2013.01); *C08F 122/14* (2013.01); *H01L 51/004* (2013.01); *H01L 51/0043* (2013.01)

(58) Field of Classification Search
CPC . C07D 209/24; C07F 7/0838; H01L 51/5253; H01L 51/004; H01L 51/0043; C08F 122/14
See application file for complete search history.

(56) References Cited

U.S. PATENT DOCUMENTS

2004/0122186 A1* 6/2004 Herr ..................... C08G 59/306
525/476

FOREIGN PATENT DOCUMENTS

| JP | 2006-117790 A | | 5/2006 |
|---|---|---|---|
| KR | 10-2011-0071039 A | | 6/2011 |
| KR | 10-2016-0150258 A | | 12/2016 |
| KR | 10-2016-0150259 | * | 12/2016 |
| KR | 10-2016-0150259 A | | 12/2016 |
| KR | 10-2017-0034045 A | | 3/2017 |
| KR | 10-2017-0077817 | * | 7/2017 |
| KR | 10-2017-0077817 A | | 7/2017 |
| SU | 653269 | * | 3/1979 |

OTHER PUBLICATIONS

Machine English Tranlsation of SU-653269 to Minakova. Mar. 1979.*
Written Opinion of the International Searching Authority, and International Search Report of corresponding PCT/KR2018/007657, dated Oct. 2, 2018, with corresponding English translations, 17 pages.

* cited by examiner

*Primary Examiner* — D Margaret M Seaman
(74) *Attorney, Agent, or Firm* — Lewis Roca Rothgerber Christie LLP

(57) ABSTRACT

Provided are: a composition for an organic light emitting diode comprising an indole-based photocurable monomer, a non-indole-based photocurable monomer, and an initiator, and an organic light emitting display manufactured therefrom.

18 Claims, 1 Drawing Sheet

【FIG. 1】
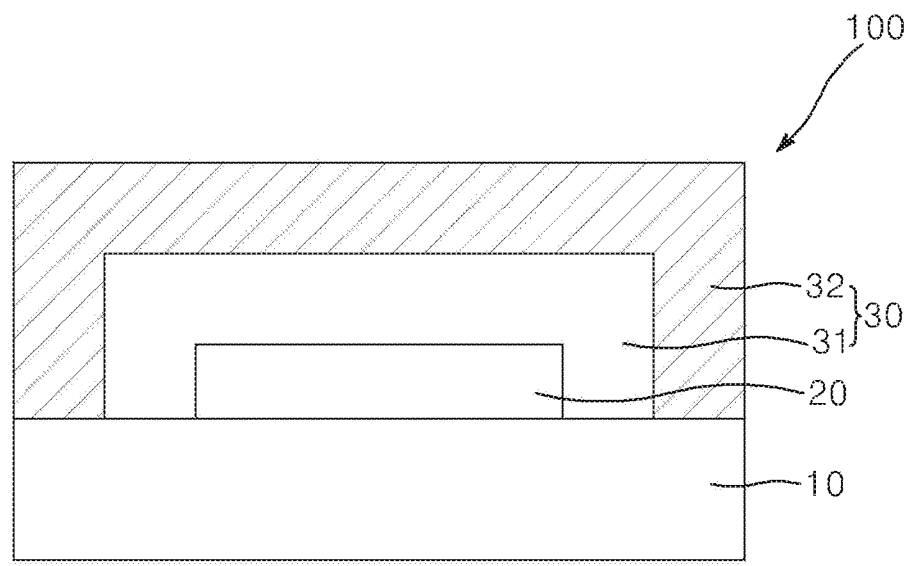
【FIG. 2】
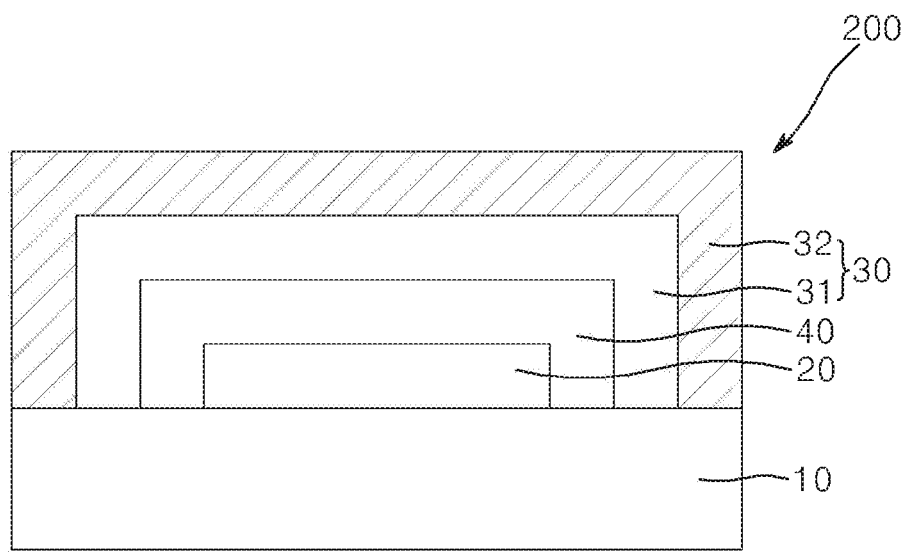

COMPOSITION FOR ORGANIC LIGHT EMITTING DIODE ENCAPSULATION AND ORGANIC LIGHT EMITTING DIODE DISPLAY MANUFACTURED THEREFROM

CROSS-REFERENCE TO RELATED APPLICATIONS

This application is a U.S. National Phase Patent Application of International Application Number PCT/KR2018/007657, filed on Jul. 5, 2018, which claims priority to Korean Patent Application Number 10-2017-0093003, filed on Jul. 21, 2017, the entire contents of both of which are incorporated herein by reference.

TECHNICAL FIELD

The present invention relates to a composition for encapsulating an organic light emitting diode and an organic light emitting diode display manufactured using the same.

BACKGROUND ART

An organic light emitting diode display is a luminous display and includes an organic light emitting diode(s). Since the organic light emitting diode can suffer from deterioration in luminous properties upon contact with external moisture or oxygen, the organic light emitting diode must be encapsulated with an encapsulation composition. The organic light emitting diode is encapsulated in a multilayer structure including an inorganic barrier layer and an organic barrier layer. The inorganic barrier layer is formed by plasma deposition, in which the organic barrier layer can be etched by plasma. If the organic barrier layer is etched, an encapsulation function of the organic barrier layer can be damaged, thereby causing deterioration in luminous properties and reliability of the light emitting diode.

On the other hand, the organic light emitting diode display is inevitably exposed to external light including UV light in use. The organic light emitting diode display can suffer from discoloration and reduction in lifespan due to damage to an organic light emitting material when exposed to UV light for a long period of time. Accordingly, a composition for encapsulating an organic light emitting diode can be used to prevent the damage to the organic light emitting diode by blocking UV light.

Korean Patent Laid-open Publication No 2011-0071039 discloses a method for sealing an organic light emitting diode.

DISCLOSURE

Technical Problem

On object of the present invention is to provide a composition for encapsulating an organic light emitting diode, which can suppress damage to the organic light emitting diode and extend lifespan of the organic light emitting diode by efficiently blocking UV light having a wavelength of 420 nm or less.

Another object of the present invention is to provide a composition for encapsulating an organic light emitting diode, which can realize an organic barrier layer having high resistance to plasma so as to improve reliability of the organic light emitting diode.

A further object of the present invention is to provide a composition for encapsulating an organic light emitting diode, which can realize an organic barrier layer having a high photocuring rate.

Technical Solution

In accordance with one aspect of the present invention, a composition for encapsulating an organic light emitting diode includes an indole based photocurable monomer, a non-indole based photocurable monomer, and an initiator.

In accordance with another aspect of the present invention, an organic light emitting diode display includes an organic light emitting diode and a barrier stack formed on the organic light emitting diode and including an inorganic barrier layer and an organic barrier layer, wherein the organic barrier layer is formed of the composition for encapsulating an organic light emitting diode according to the present invention.

Advantageous Effects

The present invention provides a composition for encapsulating an organic light emitting diode, which can suppress damage to the organic light emitting diode and extend lifespan of the organic light emitting diode by efficiently blocking UV light having a wavelength of 420 nm or less.

The present invention provides a composition for encapsulating an organic light emitting diode, which can realize an organic barrier layer having high resistance to plasma to improve reliability of an organic light emitting diode.

The present invention provides a composition for encapsulating an organic light emitting diode, which can realize an organic barrier layer having a high photocuring rate.

BRIEF DESCRIPTION OF THE DRAWINGS

FIG. 1 is a cross-sectional view of an organic light emitting diode display according to one embodiment of the present invention.

FIG. 2 is a cross-sectional view of an organic light emitting diode display according to another embodiment of the present invention.

BEST MODE

Embodiments of the present invention will be described in detail with reference to the accompanying drawings. It should be understood that the present invention may be embodied in different ways and should not limited to the following embodiments. In the drawings, portions irrelevant to the description will be omitted for clarity. Like components will be denoted by like reference numerals throughout the specification.

Herein, the term "(meth)acryl" may refer to "acryl" and/or "methacryl".

Herein, unless otherwise stated, the term "substituted" means that at least one hydrogen atom of a functional group is substituted with a halogen (F, Cl, Br or I), a hydroxyl group, a nitro group, a cyano group, an imino group (=NH, =NR, R being a $C_1$ to $C_{10}$ alkyl group), an amino group (—$NH_2$, —NH(R'), —N(R")(R'"), R', R" and R'" being independently a $C_1$ to $C_{10}$ alkyl group), an amidino group, a hydrazine or hydrazone group, a carboxyl group, a $C_1$ to $C_{20}$ alkyl group, a $C_6$ to $C_{30}$ aryl group, a $C_3$ to $C_{30}$ cycloalkyl group, a $C_3$ to $C_{30}$ heteroaryl group, or a $C_2$ to $C_{30}$ heterocycloalkyl group.

Herein, the term "aryl group" refers to a functional group in which all elements of a cyclic substituent have p-orbitals, and these p-orbitals are conjugated. The aryl group includes monocyclic, non-fused polycyclic or fused polycyclic functional groups. Here, the term "fused" means that a pair of carbon atoms is shared by contiguous rings. The aryl group also includes biphenyl groups, terphenyl groups, or quaterphenyl groups, in which at least two aryl groups are connected to each other through a sigma bond. The aryl group may refer to a phenyl group, a naphthyl group, an anthracenyl group, a phenanthrenyl group, a pyrenyl group, a chrysenyl group, and the like.

Herein, the term "alkyleneoxy group" refers to a functional group in which at least one alkylene group is linked to at least one oxygen atom. For example, the alkyleneoxy group may include an (alkylene group-oxygen atom)$_n$-alkylene group, an (alkylene group-oxygen atom-alkylene)$_n$-alkylene group, an alkylene group-oxygen atom, or an -(oxygen atom-alkylene group)$_n$-, n may be an integer of 1 to 10.

A (encapsulation) composition for encapsulating an organic light emitting diode according to one embodiment of the present invention may include an indole based photocurable monomer, a non-indole based photocurable monomer, and an initiator. With the indole based photocurable monomer, the encapsulation composition can reduce light transmittance with respect to UV light having a wavelength of 420 nm or less, preferably 410 nm or less, thereby minimizing damage to the organic light emitting diode so as to improve lifespan of the organic light emitting diode. With the indole based photocurable monomer, the encapsulation composition can realize an organic barrier layer having high resistance to plasma to improve lifespan and reliability of the organic light emitting diode. The indole based photocurable monomer contains a photocurable functional group so as to be cured together with the non-indole based photocurable monomer, thereby improving the photocuring rate of the encapsulation composition. A composition for encapsulating an organic light emitting diode, which includes an indole based UV absorbent free from an indole based photocurable monomer and a photocurable functional group, can suffer from outgassing and deterioration in panel reliability due to the presence of unreacted molecules.

According to the present invention, the indole based photocurable monomer, the non-indole based photocurable monomer, and the initiators are different compounds. Now, the indole based photocurable monomer, the non-indole based photocurable monomer, and the initiator will now be described in more detail.

Indole Based Photocurable Monomer

The indole based photocurable monomer has an indole functional group and a photocurable functional group. Preferably, a cyano (CN) group-coupled vinyl group is coupled to the indole functional group.

The indole based photocurable monomer absorbs light having a wavelength of 420 nm or less, preferably 410 nm or less, more preferably 405 nm or less, thereby reducing light transmittance at the corresponding wavelength to suppress damage to an organic light emitting diode, particularly a blue light emitting diode. A cured product obtained by curing the encapsulation composition according to the present invention has a light transmittance of 20% or less, preferably 15% or less, more preferably 10% or less, at a wavelength of 420 nm or less, preferably 410 nm or less, more preferably 405 nm. Within this range of light transmittance, the encapsulation composition can sufficiently suppress damage to the organic light emitting diode. A number of absorbents capable of absorbing light in the above wavelength range are well-known in the art. However, with the indole based photocurable monomer according to the present invention, the encapsulation composition can have significantly low light transmittance in the above wavelength range and can exhibit plasma resistance described below. In addition, when a photoinitiator is used as the initiator, the photoinitiator does not obstruct UV absorption upon curing of the encapsulation composition through UV irradiation, thereby sufficiently improving the photocuring rate of the encapsulation composition. The encapsulation composition according to the present invention may have a photocuring rate of 85% or more, preferably 90% or more. Within this range of photocuring rate, the encapsulation composition can have low shrinkage stress after curing to form a layer in which a shift does not occur, and thus can be used for encapsulation of an organic light emitting diode.

The indole based photocurable monomer can form an organic barrier layer having good plasma resistance, thereby improving lifespan and reliability of the organic light emitting diode. A cured product obtained by curing the encapsulation composition according to the present invention has a plasma etching rate of 7% or less. Within this range, the encapsulation composition can prevent an organic barrier layer from being removed by plasma etching upon formation of an inorganic barrier layer on the organic barrier layer, thereby improving reliability of the organic light emitting diode.

In one embodiment, the indole based photocurable monomer may be represented by Formula 1:

<Formula 1>

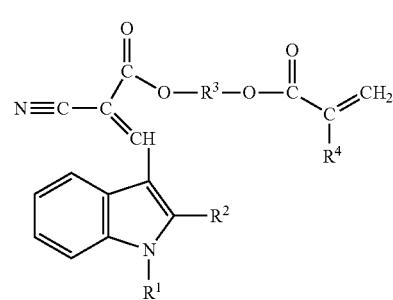

wherein in Formula 1, $R^1$ is a substituted or unsubstituted $C_1$ to $C_{10}$ alkyl group, a substituted or unsubstituted $C_6$ to $C_{20}$ aryl group, or a substituted or unsubstituted $C_7$ to $C_{20}$ arylalkyl group, $R^2$ is a substituted or unsubstituted $C_6$ to $C_{20}$ aryl group, $R^3$ is a substituted or unsubstituted $C_1$ to $C_{10}$ alkylene group, or a substituted or unsubstituted $C_1$ to $C_{10}$ alkyleneoxy group, and $R^4$ is a hydrogen atom or a substituted or unsubstituted $C_1$ to $C_5$ alkyl group.

Specifically, in Formula 1, $R^1$ may be a substituted or unsubstituted $C_1$ to $C_{10}$ alkyl group, preferably a substituted or unsubstituted $C_1$ to $C_5$ alkyl group. Specifically, in Formula 1, $R^2$ may be a substituted or unsubstituted $C_6$ to $C_{18}$ aryl group, preferably a substituted or unsubstituted $C_6$ to $C_{12}$ aryl group. Specifically, in Formula 1, $R^3$ may be a substituted or unsubstituted $C_1$ to $C_5$ alkylene group or a substituted or unsubstituted $C_1$ to $C_{10}$ alkyleneoxy group, for example, (alkylene group-oxygen atom)$_n$-alkylene group, where n is an integer of 1 to 10.

Specifically, the monomer of Formula 1 may be represented by any one of <Formula 1-1> to <Formula 1-4>:

<Formula 1-1>

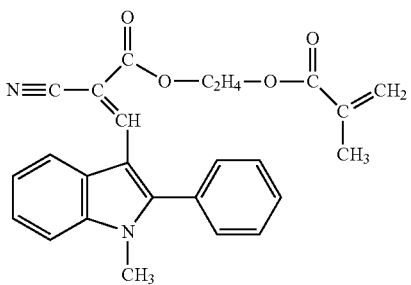

<Formula 1-2>

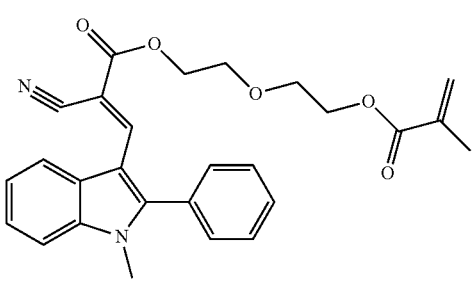

<Formula 1-3>

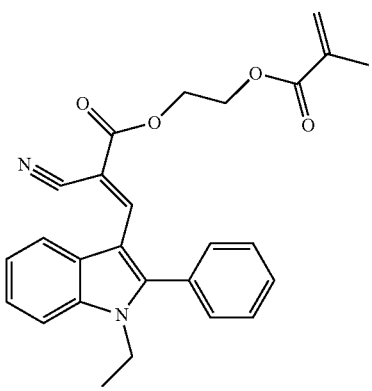

<Formula 1-4>

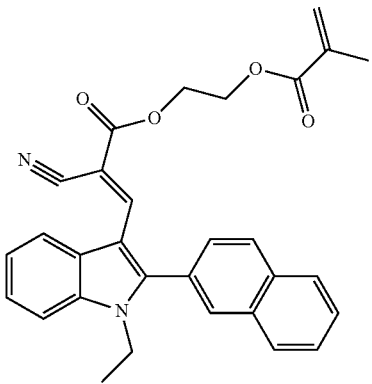

The monomer of Formula 1 may be prepared using a commercially available reaction material by a method described in Preparative Example 1.

The indole based photocurable monomer may be present in an amount of 1 wt % to 10 wt %, preferably 1 wt % to 7 wt %, more preferably 2 wt % to 5 wt %, based on the total amount of the indole based photocurable monomer, the non-indole based photocurable monomer, and the initiator. Within this range, the indole based photocurable monomer can reduce light transmittance of the encapsulation composition in the above wavelength range, thereby preventing damage to the organic light emitting diode while improving plasma resistance.

Non-Indole Based Photocurable Monomer

The non-indole based photocurable monomer may include a photocurable monomer excluding the indole based photocurable monomer. The non-indole based photocurable monomer is free from an indole group and can mean a monomer having a photocurable functional group (for example, a (meth)acrylate group, a vinyl group, and the like).

The non-indole based photocurable monomer may be a monofunctional monomer, a polyfunctional monomer, or a mixture thereof. Herein, "monofunctional monomer" may mean a monomer having a single photocurable functional group. Herein, the "polyfunctional monomer" may mean a monomer having two or more photocurable functional groups, preferably two to six photocurable functional groups. Preferably, the non-indole based photocurable monomer includes a mixture of the monofunctional monomer and the polyfunctional monomer.

The monofunctional monomer can improve the photocuring rate of the encapsulation composition. In addition, the monofunctional monomer can improve light transmittance of an organic barrier layer while reducing viscosity of the encapsulation composition.

The monofunctional monomer may include at least one of (B1) an aromatic mono(meth)acrylate containing an aromatic group and (B2) a non-aromatic mono(meth)acrylate free from an aromatic group. Preferably, the monofunctional monomer is the aromatic mono(meth)acrylate (B1) alone. Preferably, the monofunctional monomer is a mixture of the aromatic mono(meth)acrylate (B1) and the non-aromatic mono(meth)acrylate (B2).

The aromatic mono(meth)acrylate (B1) may include an aromatic group-containing mono(meth)acrylate. The aromatic mono(meth)acrylate (B1) may include a substituted or unsubstituted aromatic group-containing mono(meth)acrylate. Here, the term "aromatic group" means a monocyclic aromatic group or a polycyclic aromatic group including fused forms and the like, or means a form in which single rings are connected to each other by a sigma bond. Herein, the aromatic group is a non-indole based group free from an indole group. For example, the aromatic group may include at least one of a substituted or unsubstituted $C_6$ to $C_{50}$ aryl group, a substituted or unsubstituted $C_7$ to $C_{50}$ arylalkyl group, a substituted or unsubstituted $C_3$ to $C_{50}$ heteroaryl group, and a substituted or unsubstituted $C_3$ to $C_{50}$ heteroarylalkyl group. More specifically, the aromatic group may include at least one of phenyl, biphenyl, terphenyl, quaterphenyl, naphthyl, anthracenyl, phenanthrenyl, chrysenyl, triphenylenyl, tetracenyl, pyrenyl, benzopyrenyl, pentacenyl, coronenyl, ovalenyl, corannulenyl, benzyl, pyridinyl, pyrazinyl, pyrimidinyl, pyridazinyl, triazinyl, quinolinyl, isoquinolinyl, quinoxalinyl, acridinyl, quinazolinyl, cinnolinyl, phthalazinyl, thiazolyl, benzothiazolyl, isoxazolyl, benzisoxazolyl, oxazolyl, benzoxazolyl, pyrazolyl, indazolyl, imidazolyl, benzimidazolyl, purinyl, thiophenyl, benzothiophenyl, furanyl, benzofuranyl, and isobenzofuranyl groups.

For example, the aromatic mono(meth)acrylate (B1) may be represented by Formula 2:

<Formula 2>

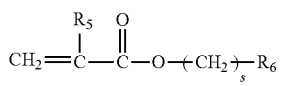

wherein in Formula 2, $R_5$ is a hydrogen atom or a methyl group, s is an integer of 0 to 10, and $R_6$ is a substituted or unsubstituted $C_6$ to $C_{50}$ aryl group or a substituted or unsubstituted $C_6$ to $C_{50}$ aryloxy group.

For example, $R_6$ may be a phenylphenoxyethyl group, a phenoxyethyl group, a benzyl group, a phenyl group, a phenylphenoxy group, a phenoxy group, a phenylethyl group, a phenylpropyl group, a phenylbutyl group, a methylphenylethyl group, a propylphenylethyl group, a methoxyphenylethyl group, a cyclohexylphenylethyl group, a chlorophenylethyl group, a bromophenylethyl group, a methylphenyl group, a methylethylphenyl group, a methoxyphenyl group, a propylphenyl group, a cyclohexylphenyl group, a chlorophenyl group, a bromophenyl group, a phenylphenyl group, a biphenyl group, a terphenyl group, a quaterphenyl group, an anthracenyl group, a naphthalenyl group, a triphenylenyl group, a methylphenoxy group, an ethylphenoxy group, a methylethylphenoxy group, a methoxyphenyloxy group, a propylphenoxy group, a cyclohexylphenoxy group, a chlorophenoxy group, a bromophenoxy group, a biphenyloxy group, a terphenyloxy group, a quaterphenyloxy group, an anthracenyloxy group, a naphthalenyloxy group, or a triphenylenyloxy group.

Specifically, the aromatic mono(meth)acrylate (B1) may include at least one of 2-phenylphenoxyethyl (meth)acrylate, phenoxyethyl (meth)acrylate, phenyl (meth)acrylate, phenoxy (meth)acrylate, 2-ethylphenoxy (meth)acrylate, benzyl (meth)acrylate, 2-phenylethyl (meth)acrylate, 3-phenylpropyl (meth)acrylate, 4-phenylbutyl (meth)acrylate, 2-(2-methylphenyl)ethyl (meth)acrylate, 2-(3-methylphenyl)ethyl (meth)acrylate, 2-(4-methylphenyl)ethyl (meth)acrylate, 2-(4-propylphenyl)ethyl (meth)acrylate, 2-(4-(1-methylethyl)phenyl)ethyl (meth)acrylate, 2-(4-methoxyphenyl)ethyl (meth)acrylate, 2-(4-cyclohexylphenyl)ethyl (meth)acrylate, 2-(2-chlorophenyl)ethyl (meth)acrylate, 2-(3-chlorophenyl)ethyl (meth)acrylate, 2-(4-chlorophenyl)ethyl (meth)acrylate, 2-(4-bromophenyl)ethyl (meth)acrylate, 2-(3-phenylphenyl)ethyl (meth)acrylate, 4-(biphenyl-2-yloxy)butyl (meth)acrylate, 3-(biphenyl-2-yloxy)butyl (meth)acrylate, 2-(biphenyl-2-yloxy)butyl (meth)acrylate, 1-(biphenyl-2-yloxy)butyl (meth)acrylate, 4-(biphenyl-2-yloxy)propyl (meth)acrylate, 3-(biphenyl-2-yloxy)propyl (meth)acrylate, 2-(biphenyl-2-yloxy)propyl (meth)acrylate, 1-(biphenyl-2-yloxy)propyl (meth)acrylate, 4-(biphenyl-2-yloxy)ethyl (meth)acrylate, 3-(biphenyl-2-yloxy)ethyl (meth)acrylate, 2-(biphenyl-2-yloxy)ethyl (meth)acrylate, 1-(biphenyl-2-yloxy)ethyl (meth)acrylate, 2-(4-benzylphenyl)ethyl (meth)acrylate, 1-(4-benzylphenyl)ethyl (meth)acrylate, and structural isomers thereof, without being limited thereto. That is, it should be understood that the (meth)acrylates as set forth herein are provided by way of example only and the present invention is not limited thereto. Further, the (meth)acrylates according to the present invention include all acrylates corresponding to structural isomers thereof. For example, although only 2-phenylethyl (meth)acrylate is mentioned above by way of example, the (meth)acrylates according to the present invention include all of 3-phenylethyl (meth)acrylate and 4-phenyl (meth)acrylate.

Specifically, in Formula 2, s may be an integer of 1 to 5 and $R_6$ may be a substituted or unsubstituted phenylphenoxy group, a substituted or unsubstituted phenylphenylthiol group, a substituted or unsubstituted biphenylphenoxy group, or a substituted or unsubstituted terphenylphenoxy group, wherein a substituent may be a heavy hydrogen atom, a $C_1$ to $C_{10}$ alkyl group, a $C_1$ to $C_{10}$ alkoxy group, a $C_6$ to $C_{18}$ aryl group, a $C_3$ to $C_{18}$ hetero-aryl group, or a thiol group.

The aromatic mono(meth)acrylate (B1) may be present in an amount of 10 wt % to 50 wt %, for example, 15 wt % to 40 wt %, or 15 wt % to 35 wt %, based on the total amount of the indole based photocurable monomer, the non-indole based photocurable monomer, and the initiator. Within this range, the aromatic mono(meth)acrylate (B1) can improve plasma resistance of the encapsulation composition.

The non-aromatic mono(meth)acrylate (B2) may be a substituted or unsubstituted $C_1$ to $C_{20}$ alkyl group-containing mono(meth)acrylate. Specifically, the non-aromatic mono(meth)acrylate (B2) may be an unsubstituted linear $C_1$ to $C_{20}$ alkyl group-containing mono(meth)acrylate, more specifically an unsubstituted linear $C_{10}$ to $C_{20}$ alkyl group-containing mono(meth)acrylate. For example, the non-aromatic mono(meth)acrylate (B2) may include a least one of decyl (meth)acrylate, undecyl (meth)acrylate, lauryl (meth)acrylate, tridecyl (meth)acrylate, tetradecyl (meth)acrylate, pentadecyl (meth)acrylate, hexadecyl (meth)acrylate, heptadecyl (meth)acrylate, octadecyl (meth)acrylate, nonadecyl (meth)acrylate, and arachidyl (meth)acrylate, without being limited thereto.

The non-aromatic mono(meth)acrylate (B2) may be optionally present in an amount of 0 wt % to 30 wt % or less, for example, 0 wt % to 20 wt % or less or 0.1 wt % to 20 wt %, based on the total amount of the indole based photocurable monomer, the non-indole based photocurable monomer, and the initiator.

The monofunctional monomer may be present in an amount of 10 wt % to 60 wt %, for example, 15 wt % to 55 wt %, based on the total amount of the indole based photocurable monomer, the non-indole based photocurable monomer, and the initiator. Within this range, the encapsulation composition can exhibit low viscosity and high adhesive strength.

The polyfunctional monomer can increase the photocuring rate of the encapsulation composition. The polyfunctional monomer may include at least one of a di(meth)acrylate, a tri(meth)acrylate, a tetra(meth)acrylate, a penta(meth)acrylate, and a hexa(meth)acrylate. Preferably, the polyfunctional monomer includes a di(meth)acrylate. The di(meth)acrylate may include a di(meth)acrylate alone or a mixture of (C1) a di(meth)acrylate and (C2) a di(meth)acrylate.

The di(meth)acrylate (C1) is a non-silicone based group free from silicon (Si) and may include a di(meth)acrylate, which has a substituted or unsubstituted $C_1$ to $C_{20}$ alkylene group, preferably, an unsubstituted C1 to C15 alkylene group, between (meth)acrylate groups. Here, the carbon number of the alkylene group means the number of carbon atoms in the alkylene group per se excluding carbon atoms in the di(meth)acrylate group. For example, the di(meth)acrylate (C1) may be represented by Formula 3:

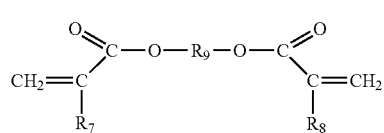

<Formula 3> wherein in Formula 3, $R_7$ and $R_8$ are independently a hydrogen atom or a methyl group, and $R_9$ is a substituted or unsubstituted $C_1$ to $C_{20}$ alkylene group.

For example, in Formula 3, $R_9$ may be an unsubstituted $C_8$ to $C_{12}$ alkylene group. More specifically, the di(meth)acrylate (C1) may include at least one of octanediol di(meth)acrylate, nonanediol di(meth)acrylate, decanediol di(meth)acrylate, undecanediol di(meth)acrylate, and dodecanediol di(meth)acrylate.

The di(meth)acrylate (C1) may be present in an amount of 10 wt % to 70 wt %, preferably 30 wt % to 70 wt %, more preferably 40 wt % to 65 wt %, based on the total amount of the indole based photocurable monomer, the non-indole based photocurable monomer, and the initiator. Within this range, the di(meth)acrylate (C1) can increase the crosslinking density of the encapsulation composition to improve strength of a layer formed of the encapsulation composition.

The di(meth)acrylate (C2) may include a silicone based di(meth)acrylate containing Si. The encapsulation composition includes a mixture of a non-silicone based di(meth)acrylate and a silicone based di(meth)acrylate as the di(meth)acrylate, thereby reducing viscosity and curing shrinkage.

The di(meth)acrylate (C2) may be represented by Formula 4:

<Formula 4>

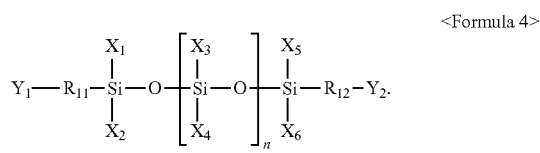

wherein in Formula 4, $R_{11}$ and $R_{12}$ are identical to or different from each other, and $R_{11}$ and $R_{12}$ are independently a single bond, a substituted or unsubstituted $C_1$ to $C_{20}$ alkylene group, a substituted or unsubstituted $C_1$ to $C_{30}$ alkylene ether group, *—N(R')—R"—* (* being a linking site of an element, R' being a substituted or unsubstituted $C_1$ to $C_{30}$ alkyl group, and R" being a substituted or unsubstituted $C_1$ to $C_{20}$ alkylene group), a substituted or unsubstituted $C_6$ to $C_{30}$ arylene group, a substituted or unsubstituted $C_7$ to $C_{30}$ arylalkylene group, or *—O—R"—* (* being a linking site of an element and R" being a substituted or unsubstituted $C_1$ to $C_{20}$ alkylene group), $X_1$, $X_2$, $X_3$, $X_4$, $X_5$ and $X_6$ are identical to or different from each other, and $X_1$, $X_2$, $X_3$, $X_4$, $X_5$ and $X_6$ are independently a hydrogen atom, a substituted or unsubstituted $C_1$ to $C_{30}$ alkyl group, a substituted or unsubstituted $C_1$ to $C_{30}$ alkyl ether group, *—N(R')(R") (* being a linking site of an element, and R' and R" being identical to or different from each other and being independently a hydrogen atom or a substituted or unsubstituted $C_1$ to $C_{30}$ alkyl group), a substituted or unsubstituted $C_1$ to $C_{30}$ alkylsulfide group, a substituted or unsubstituted $C_6$ to $C_{30}$ aryl group, or a substituted or unsubstituted $C_7$ to $C_{30}$ arylalkyl group, where at least one of $X_1$, $X_2$, $X_3$, $X_4$, $X_5$ and $X_6$ is a substituted or unsubstituted $C_6$ to $C_{30}$ aryl group, and $Y_1$ and $Y_2$ are identical to or different from each other, and $Y_1$ and $Y_2$ are independently represented by Formula 5:

<Formula 5>

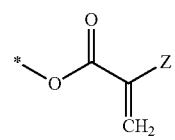

wherein in Formula 5,

* is a linking site of an element, Z is a hydrogen atom or a substituted or unsubstituted $C_1$ to $C_{30}$ alkyl group), and n is an integer of 0 to 30 or has an average value of 0 to 30.

Here, the term "single bond" refers to a direct bond ($Y_1$—Si) between Si and $Y_1$ without any intervening element therebetween or a direct bond (Si—$Y_2$) between Si and $Y_2$ without any intervening element therebetween.

Specifically, $R_{11}$ and $R_{12}$ may be independently a $C_1$ to $C_5$ alkylene group or a single bond. Specifically, $X_1$, $X_2$, $X_3$, $X_4$, $X_5$ and $X_6$ may be independently a $C_1$ to $C_5$ alkyl group or a $C_6$ to $C_{10}$ aryl group, wherein at least one of $X_1$, $X_2$, $X_3$, $X_4$, $X_5$ and $X_6$ may be a $C_6$ to $C_{10}$ aryl group. More specifically, $X_1$, $X_2$, $X_3$, $X_4$, $X_5$ and $X_6$ may be independently a $C_1$ to $C_5$ alkyl group or a $C_6$ to $C_{10}$ aryl group, wherein one, two, three or six of $X_1$, $X_2$, $X_3$, $X_4$, $X_5$ and $X_6$ may be a $C_6$ to $C_{10}$ aryl group. More specifically, $X_1$, $X_2$, $X_3$, $X_4$, $X_5$ and $X_6$ may be independently a methyl group, an ethyl group, a propyl group, a butyl group, a pentyl group, a phenyl group, or a naphthyl group, wherein one, two, three or six of $X_1$, $X_2$, $X_3$, $X_4$, $X_5$ and $X_6$ may be independently a phenyl group or a naphthyl group. Specifically, n may be an integer of 1 to 5.

Specifically, the di(meth)acrylate (C2) may be represented by anyone of the following Formulae 4-1 to 4-6.

<Formula 4-1>

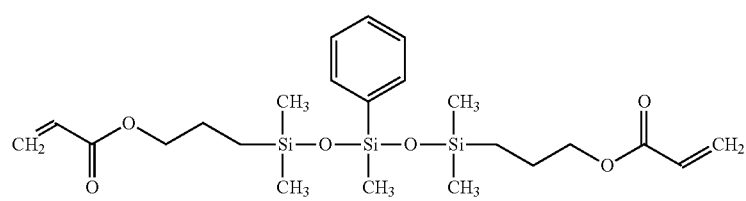

-continued

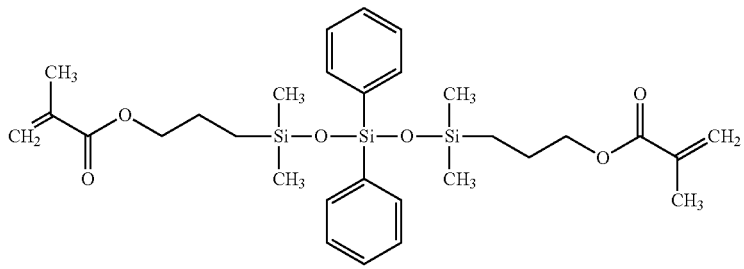

<Formula 4-2>

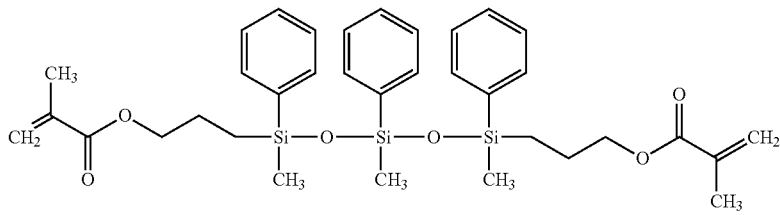

<Formula 4-3>

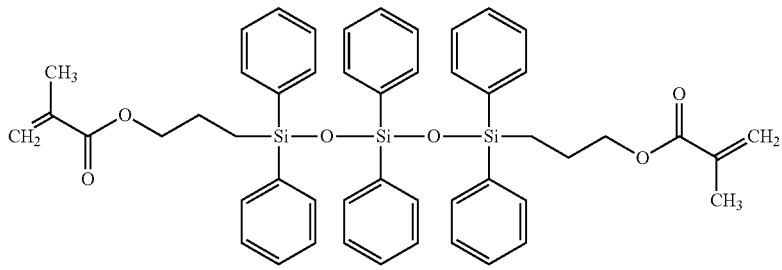

<Formula 4-4>

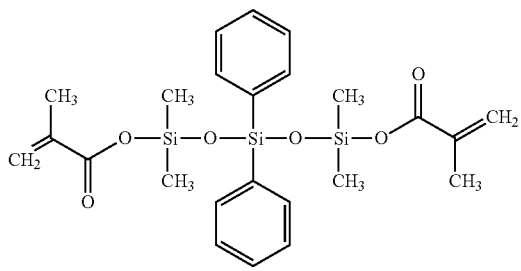

<Formula 4-5>

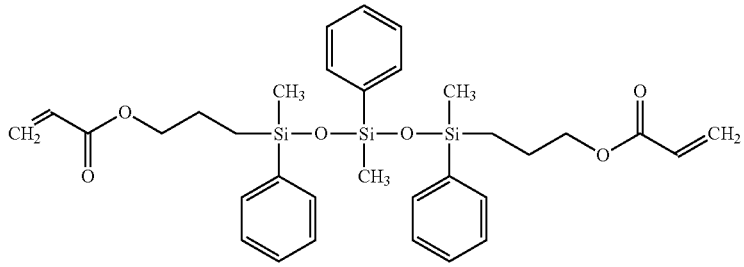

<Formula 4-6>

The di(meth)acrylate (C2) may have a weight average molecular weight of 100 g/mol to 2,000 g/mol, specifically 200 g/mol to 1,000 g/mol. Within this range, the encapsulation composition exhibits good deposition characteristics and can realize an organic barrier layer having a low plasma etching rate.

The di(meth)acrylate (C2) may be prepared by a typical method or may be obtained from commercially available products. For example, the di(meth)acrylate (C2) may be prepared by reacting a siloxane compound containing an aryl group having at least one silicone bond with a compound for extending the carbon number (for example: allyl alcohol), followed by reacting with (meth)acryloyl chloride, without being limited thereto. Alternatively, the di(meth)acrylate (C2) may be prepared by reacting a siloxane compound containing an aryl group having at least one silicone bond with (meth)acryloyl chloride, without being limited thereto.

The di(meth)acrylate (C2) may be optionally present in an amount of 0 wt % to 30 wt % or less, preferably 0.1 wt % to 30 wt %, based on the total amount of the indole based photocurable monomer, the non-indole based photocurable monomer, and the initiator.

The tri(meth)acrylate may include tri(meth)acrylates of $C_3$ to $C_{20}$ triol, tetraol, pentaol or hexaol, such as trimethylolpropane tri(meth)acrylate, pentaerythritol tri(meth)acrylate, dipentaerythritol tri(meth)acrylate, and the like. The tetra(meth)acrylate may include tetra(meth)acrylates of $C_4$ to $C_{20}$ tetraol, pentaol or hexaol, such as pentaerythritol tetra(meth)acrylate, dipentaerythritol tetra(meth)acrylate, and the like. The penta(meth)acrylate may include penta(meth)acrylates of $C_4$ to $C_{20}$ pentaol or hexaol, such as dipentaerythritol penta(meth)acrylate, and the like. The hexa(meth)acrylate may include hexa(metah)acrylates of $C_4$ to $C_{20}$ hexaol, such as dipentaerythritol hexa(meth)acrylate and the like.

The polyfunctional monomer may be present in an amount of 10 wt % to 80 wt %, for example, 20 wt % to 80 wt %, or 40 wt % to 80 wt %, based on the total amount of the indole based photocurable monomer, the non-indole based photocurable monomer, and the initiator. Within this range, the polyfunctional monomer can increase the crosslinking density of the encapsulation composition to improve strength of a layer formed of the encapsulation composition.

The non-indole based photocurable monomer may be present in an amount of 50 wt % to 98 wt %, preferably 90 wt % to 95 wt %, based on the total amount of the indole based photocurable monomer, the non-indole based photocurable monomer, and the initiator. Within this range, the non-indole based photocurable monomer can reduce light transmittance within the above wavelength range, thereby preventing damage to the organic light emitting diode while improving plasma resistance of the encapsulation composition.

The non-indole based photocurable monomer may include the monofunctional monomer and the polyfunctional monomer in a weight ratio of 1:0.5 to 1:10, preferably 1:0.5 to 1:5. Within this range, the non-indole based photocurable monomer can increase the curing rate of the organic barrier layer and can secure a suitable range of viscosity to improve coatability of the encapsulation composition.

Initiator

The initiator may include any typical photopolymerization initiators capable of photocuring reaction. For example, the photopolymerization initiator may include a triazine initiator, an acetophenone initiator, a benzophenone initiator, a thioxanthone initiator, a benzoin initiator, a phosphorus initiator, an oxime initiator, or mixtures thereof.

The phosphorus initiator may include diphenyl(2,4,6-trimethylbenzoyl)phosphine oxide, benzyl(diphenyl)phosphine oxide, bis(2,6-dimethoxybenzoyl)(2,4,4-trimethylpentyl)phosphine oxide, or mixtures thereof. For example, the phosphorus initiator can exhibit better initiation performance under UV light of long wavelengths in the encapsulation composition according to the present invention. These initiators may be used alone or as a mixture thereof.

In the encapsulation composition, the initiator may be present in an amount of 1 wt % to 40 wt %, specifically 1 wt % to 10 wt %, 1 wt % to 9 wt %, or 1 wt % to 8 wt %, based on the total amount of the indole based photocurable monomer, the non-indole based photocurable monomer, and the initiator. Within this range, the initiator allows sufficient photopolymerization upon exposure to light and can prevent deterioration in light transmittance due to unreacted initiator remaining after photopolymerization.

The encapsulation composition according to the present invention may be prepared by mixing the indole based photocurable monomer, the non-indole based photocurable monomer and the initiator. The encapsulation composition may be formed as a solvent-free composition not containing a solvent. For example, when the encapsulation composition is a solvent-free composition, wt % is based on the total weight of the indole based photocurable monomer, the non-indole based photocurable monomer and the initiator.

The encapsulation composition according to the present invention is a photocurable composition and may be cured by irradiation with UV light at 10 to 500 mW/cm$^2$ for 1 to 50 seconds.

The encapsulation composition may have a viscosity at 25° C.±2° C. of about 7 cP to 50 cP. Within this range, the encapsulation composition allows easy formation of an organic barrier layer through deposition thereof.

The encapsulation composition may be used in encapsulation of an organic light emitting diode. Specifically, the encapsulation composition may form organic barrier layers in an encapsulation structure wherein inorganic barriers and the organic barrier layers are sequentially stacked one above another. Particularly, the encapsulation composition may be used in a flexible organic light emitting diode display.

The encapsulation composition may be used in encapsulation of a member for an apparatus, particularly, a member for displays, which can suffer from degradation or deterioration in quality due to permeation of gas or liquid in a surrounding environment, for example, atmospheric oxygen and/or moisture and/or water vapor and due to permeation of chemicals used in the preparation of electronic products. Examples of the member for an apparatus may include illumination devices, metal sensor pads, microdisc lasers, electrochromic devices, photochromic devices, microelectromechanical systems, solar cells, integrated circuits, charge coupled devices, light emitting polymers, light emitting diodes, and the like, without being limited thereto.

An organic light emitting diode display according to the present invention may include an organic barrier layer formed of the encapsulation composition for encapsulating an organic light emitting diode according to the embodiments of the present invention. Specifically, the organic light emitting diode display may include an organic light emitting diode and a barrier stack formed on the light emitting device and including an inorganic barrier layer and an organic barrier layer, in which the organic barrier layer may be formed of the encapsulation composition according to the embodiments of the present invention. As a result, the organic light emitting diode display can exhibit high reliability.

Next, an organic light emitting diode display according to one embodiment of the present invention will be described with reference to FIG. 1. FIG. 1 is a cross-sectional view of an organic light emitting diode display according to one embodiment of the present invention.

Referring to FIG. 1, an organic light emitting diode display 100 according to this embodiment includes a substrate 10, an organic light emitting diode 20 formed on the substrate 10, and a barrier stack 30 formed on the organic light emitting diode 20 and including an inorganic barrier layer 31 and an organic barrier layer 32, wherein the inorganic barrier layer 31 adjoins the organic light emitting diode 20, and the organic barrier layer 32 may be formed of the encapsulation composition for encapsulating an organic light emitting diode according to the embodiments of the present invention.

The substrate 10 may be selected from any substrate so long as an organic light emitting diode can be formed on the substrate 10. For example, the substrate 10 may be formed of a material, such as transparent glass, a plastic sheet, and a silicon or metal substrate.

The organic light emitting diode 20 is commonly used in an organic light emitting diode display, and, although not shown in FIG. 1, may include a first electrode, a second electrode, and an organic light emitting layer formed between the first electrode and the second electrode. In addition, the organic light emitting layer may have a structure wherein a hole injection layer, a hole transport layer, a light emitting layer, an electron transport layer, and an electron injection layer are sequentially stacked, without being limited thereto.

The barrier stack 30 includes the inorganic barrier layer 31 and the organic barrier layer 32, and the inorganic and organic barrier layers 31, 32 are composed of different components, thereby realizing the functions of encapsulating the organic light emitting diode.

The inorganic barrier layer 31 includes different components than the organic barrier layer 32, thereby supplementing the effects of the organic barrier layer 32. The inorganic barrier layer 31 may be formed of inorganic materials having good light transmittance and good moisture and/or oxygen barrier properties. For example, the inorganic barrier layer 31 may include at least one selected from among metals; nonmetals; compounds or alloys of at least two metals; compounds or alloys of at least two nonmetals; oxides of metals, nonmetals or mixtures thereof; fluorides of metals or nonmetals or mixtures thereof; nitrides of metals, nonmetals or mixtures thereof; carbides of metals, nonmetals or mixtures thereof; oxynitrides of metals, nonmetals or mixtures thereof; borides of metals, nonmetals or mixtures thereof; oxyborides of metals, nonmetals or mixtures thereof; silicides of metals, nonmetals or mixtures thereof; and mixtures thereof. The metals or nonmetals may include silicon (Si), aluminum (Al), selenium (Se), zinc (Zn), antimony (Sb), indium (In), germanium (Ge), tin (Sn), bismuth (Bi), transition metals, and lanthanide metals, without being limited thereto. Specifically, the inorganic barrier layer may be silicon oxide ($SiO_x$), silicon nitride ($SiN_x$), silicon oxynitride ($SiO_xN_y$), zinc selenide (ZnSe), zinc oxide (ZnO), antimony trioxide ($Sb_2O_3$), aluminum oxide ($AlO_x$) including alumina ($Al_2O_3$), indium oxide ($In_2O_3$), or tin oxide ($SnO_2$).

The inorganic barrier layer 31 may be deposited by a plasma process or a vacuum process, for example, sputtering, chemical vapor deposition, plasma chemical vapor deposition, evaporation, sublimation, electron cyclotron resonance-plasma enhanced chemical vapor deposition, or combinations thereof.

The organic barrier layer 32 and the inorganic barrier layer 31 are alternately deposited, thereby securing planarization properties of the inorganic barrier layer 31, while preventing defects of one inorganic barrier layer 31 from spreading to other inorganic barrier layers 31.

The organic barrier layer 32 may be formed by coating, deposition, or curing of the encapsulation composition according to the embodiments of the present invention, or combinations thereof. For example, the organic barrier layer 32 may be formed by coating the encapsulation composition to a thickness of 1 μm to 50 μm, followed by curing the encapsulation composition through irradiation at 10 mW/cm² to 500 mW/cm² for 1 second to 50 seconds.

The barrier stack 30 may include any number of the organic barrier layer 32 and the inorganic barrier layer 31. Combination of the organic barrier layer 32 and the inorganic barrier layer 31 may vary with a level of permeation resistance to oxygen and/or moisture and/or water vapor and/or chemicals. For example, the organic barrier layers 32 and the inorganic barrier layers 31 may be formed in a total of 10 layers or less, for example, 2 layers to 7 layers.

Specifically, the organic barrier layers 32 and the inorganic barrier layers 31 may be formed in a total of 7 layers in the following order: inorganic barrier layer 31/organic barrier layer 32/inorganic barrier layer 31/organic barrier layer 32/inorganic barrier layer 31/organic barrier layer 32/inorganic barrier layer 31.

In the barrier stack 30, the organic barrier layers 32 and the inorganic barrier layers 31 may be alternately deposited. This is because the aforementioned encapsulation composition has an effect on the organic barrier layer 32 due to the properties thereof. As a result, the organic barrier layer 32 and the inorganic barrier layer 31 can supplement or reinforce encapsulation of the member for the apparatus.

Next, an organic light emitting diode display according to another embodiment of the present invention will be described with reference to FIG. 2. FIG. 2 is a cross-sectional view of an organic light emitting diode display according to another embodiment of the present invention.

Referring to FIG. 2, an organic light emitting diode display 200 according to this embodiment includes a substrate 10, an organic light emitting diode 20 formed on the substrate 10, and a barrier stack 30 formed on the organic light emitting diode 20 and including an inorganic barrier layer 31 and an organic barrier layer 32, in which the inorganic barrier layer 31 encapsulates an inner space 40 which receives the organic light emitting diode 20 therein, and the organic barrier layer 32 may be formed of the encapsulation composition for encapsulating an organic light emitting diode according to the embodiments of the present invention. The organic light emitting diode display according to this embodiment is substantially the same as the organic light emitting diode display according to the above embodiment except that the inorganic barrier layer 31 does not adjoin the organic light emitting diode 20.

Next, the present invention will be described in more detail with reference to some examples. It should be understood that these examples are provided for illustration only and are not to be construed in any way as limiting the present invention.

Preparative Example 1: Preparation of Indole Based Photocurable Monomer

A compound represented by Formula 1-1 was prepared.

<Formula 1-1>

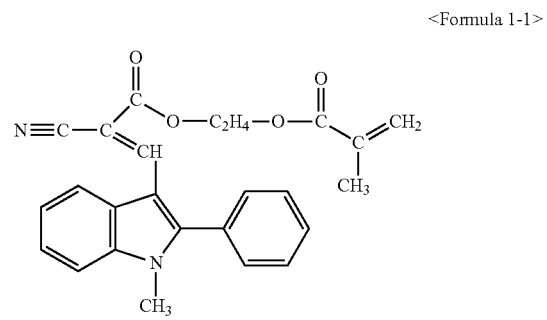

Step 1: In a 1,000 ml flask provided with a cooling tube, a Dean-Stark apparatus and a stirrer, 200 g of cyanoacetic acid, 320 g of 2-hydroxy ethyl methacrylate, 600 ml of toluene, and 3 g of concentrated sulfuric acid (Daejung Chemicals & Materials Co., Ltd.) were placed, followed by nitrogen purging for 30 minutes and heating the flask to 160° C. to remove water therefrom. The solvent was removed through distillation, thereby obtaining 2-(2-cyanoacetoxy) ethyl methacrylate (molecular weight: 197.19 g/mol) and having a purity of 96% as measured by HPLC. ($^1$H NMR: δ 6.12, s, 1H; δ 5.62, s, 1H; δ 4.45, m, 2H; δ 4.38, m, 2H; δ 3.01, s, 2H; δ 1.94, s, 3H).

Step 2: In a 500 ml flask provided with a cooling tube and a stirrer, 15.2 g of KOH, 38 g of iodomethane, 50 g of 2-phenyl 1H-Indole-3-carboxaldehyde, and 150 g of DMF (dimethylformamide) were placed and stirred at room temperature for 12 hours. The solvent was removed through distillation, thereby obtaining 1-methyl 2-phenyl 1H-indole-3-carboxaldehyde (molecular weight: 235.28 g/mol) and having a purity of 96% as measured by HPLC. (1H NMR: δ 9.76, s, 1H; δ 8.46, m, 1H; δ 7.59, m, 3H; δ 7.52, m, 2H; δ 7.42, m, 3H; δ 3.79, s, 3H)

Step 3: In a 500 ml flask provided with a cooling tube and a stirrer, 21 g of 1-methyl 2-phenyl 1H-Indole-3-carboxaldehyde obtained in Step 2, 21.2 g of 2-(2-cyanoacetoxy) ethyl methacrylate obtained in Step 1, 2.3 g of piperidine, and 230 g of pyridine were placed and stirred at room temperature for 12 hours. The solvent was removed through distillation, followed by recrystallization with ethanol, thereby obtaining a compound represented by Formula 1-1 (molecular weight: 414.45 g/mol) and having a purity of 98% as measured by HPLC. ($^1$H NMR: δ 8.46, m, 1H; δ 8.17, s, 1H; δ 7.59, m, 3H; δ 7.42, m, 5H; δ 6.15, s, 1H; δ 5.62, s, 1H; δ 4.51, m, 2H; δ 4.42, m, 2H; δ 3.75, s, 3H; δ 1.96, s, 3H)

Preparative Example 2: Preparation of Silicone Based Di(Meth)Acrylate

In a 1,000 ml flask provided with a cooling tube and a stirrer, 300 ml of ethyl acetate, 21 g of 3,3-diphenyl-1,1,5,5-tetramethyltrisiloxane and 43 g of allyl alcohol (Daejung Chemicals & Materials Co., Ltd.) were placed, followed by nitrogen purging for 30 minutes. Next, 72 ppm of Pt-on-carbon black powder (Aldrich GmbH) was added thereto, followed by heating the flask to 80° C. and stirring the components for 4 hours. The remaining solvent was removed by distillation, thereby obtaining a compound. 71.5 g of the obtained compound and 39 g of triethylamine were sequentially added to 300 ml of dichloromethane, followed by slowly adding 30.2 g of methacryloyl chloride while stirring the mixture at 0° C. The remaining solvent was removed by distillation, thereby obtaining a compound (molecular weight: 584.92 g/mol) represented by Formula 4-2 and having a purity of 96% as measured by HPLC.

($^1$H NMR: δ 7.52, m, 6H; δ 7.42, m, 4H; δ 6.25, d, 2H; δ 6.02, dd, 2H; δ 5.82, t, 1H; δ 5.59, d, 2H; δ 3.86, m, 4H; δ 1.52, m, 4H; δ 0.58, m, 4H; δ 0.04, m, 12H)

<Formula 4-2>

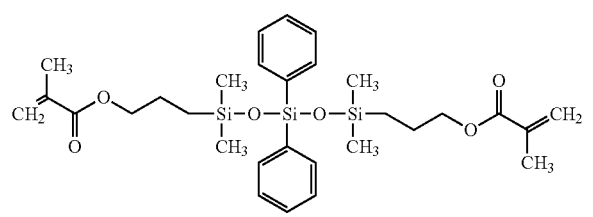

Details of components used in Examples and Comparative Examples were as follows.

(A) Indole based photocurable monomer: Photocurable monomer of Preparative Example 1;

(B) Non-indole based photocurable monomer: (B1) 2-phenylphenoxy acrylate (M1142, Miwon Co., Ltd.), (B2) lauryl acrylate (Sartomer Co., Ltd.);

(C) Non-indole based photocurable monomer: (C1) 1,2-dodecandiol diacrylate (Sartomer Co., Ltd.), (C2) Monomer of Preparative Example 2;

(D) Initiator: Darocur TPO (BASF) (phosphorus initiator);

(E) UV absorbent: BONARSORB (represented by Formula 6).

<Formula 6>

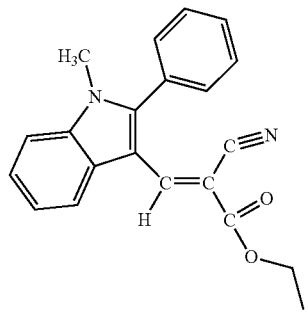

Example 1

3 parts by weight of (A) photocurable monomer of Preparative Example 1, 33 parts by weight of (B1) 2-phenylphenoxy acrylate, 61 parts by weight of (C) 1,2-dodecanediol acrylate, and 3 parts by weight of (D) initiator were placed in a 125 ml brown polypropylene bottle, and mixed by a shaker at room temperature for 3 hours, thereby obtaining an encapsulation composition.

Examples 2 to 5 and Comparative Examples 1 to 3

Encapsulation compositions were prepared in the same manner as in Example 1 except that the amounts of the components of Example 1 were changed as listed in Table 1 (unit: parts by weight).

Each of the encapsulation compositions prepared in Examples 1-5 and Comparative Examples 1-3 was evaluated as to the following properties as listed in Table 1. Results are shown in Table 1.

(1) Viscosity: The viscosity of each of the encapsulation compositions prepared in Examples 1-5 and Comparative Examples 1-3 was measured at 25° C. using a viscometer Spindle No. 40 (LV DV-II Pro, Brookfield Co., Ltd.).

(2) Photocuring rate: The intensity of absorption peaks in the vicinity of 1,635 cm$^{-1}$ (C=C) and 1,720 cm$^{-1}$ (C=O) of each of the encapsulation compositions was measured using an FT-IR spectrometer (NICOLET 4700, Thermo Co., Ltd.). Each encapsulation composition was applied to a glass substrate through a sprayer, followed by curing through UV irradiation at 100 mW/cm$^2$ for 10 seconds, thereby preparing a specimen having a size of 20 cm×20 cm×3 μm (width× length×thickness). Then, the intensity of absorption peaks of the cured film was measured in the vicinity of 1,635 (C=C) and 1,720 cm$^{-1}$ (C=O) using an FT-IR spectrometer (NICOLET 4700, Thermo Co., Ltd.). Photocuring rate was calculated by Equation 1:

Photocuring rate (%)=|1−(A/B)|100,  <Equation 1> wherein in Equation 1, A is a ratio of the intensity of an absorption peak in the vicinity of 1,635 cm$^{-1}$ to the intensity of an absorption peak in the vicinity of 1,720 cm$^{-1}$ measured for the cured film, and B is a ratio of the intensity of an absorption peak in the vicinity of 1,635 cm$^{-1}$ to the intensity of an absorption peak in the vicinity of 1,720 cm$^{-1}$ measured for the encapsulation composition).

(3) Plasma etching rate: Each of the encapsulation compositions was deposited with a predetermined thickness on a Si wafer and photocured to form an organic barrier layer, followed by measuring the initial deposition height (T1, unit: μm) of the organic barrier layer. The organic barrier layer was then subjected to induction coupled plasma (ICP) treatment under conditions of ICP power: 2,500 W, RE power: 300 W, DC bias: 200V, Ar flow: 50 sccm, etching time: 1 min, and pressure: 10 mTorr, followed by measuring the height (T2, unit: μm) of the organic barrier layer. The height (thickness) of the organic barrier layer was measured using an FE-SEM (Hitachi High Technologies Corporation). Plasma etching rate was calculated by Equation 2:

Plasma etching rate of organic barrier layer (%)= (T1−T2)/T1×100.  <Equation 2>

(4) Light transmittance: Each of the encapsulation compositions was cured through UV irradiation under $N_2$ conditions to form a 10 μm-thick film, and light transmittance thereof was measured at a wavelength of 405 nm using a Lambda 950 (Perkin Elmer Co., Ltd.).

TABLE 1

|   |    | Example |      |      |      |      | Comparative Example |      |      |
|---|----|---------|------|------|------|------|---------------------|------|------|
|   |    | 1       | 2    | 3    | 4    | 5    | 1                   | 2    | 3    |
| A |    | 3       | 3    | 3    | 5    | 2    | 0                   | 0    | 0    |
| B | B1 | 33      | 33   | 19   | 32   | 33   | 34                  | 20   | 34   |
|   | B2 | 0       | 20   | 0    | 0    | 0    | 0                   | 0    | 0    |
| C | C1 | 61      | 41   | 47   | 60   | 62   | 63                  | 48   | 62   |
|   | C2 | 0       | 0    | 28   | 0    | 0    | 0                   | 29   | 0    |
| D |    | 3       | 3    | 3    | 3    | 3    | 3                   | 3    | 3    |
| E |    | 0       | 0    | 0    | 0    | 0    | 0                   | 0    | 1    |
| Viscosity (cps, @25° C.) | | 21.2 | 15.2 | 22.6 | 21.8 | 21.0 | 20.1 | 21.4 | 21.3 |
| Photocuring rate (%) | | 91.2 | 92.3 | 92.5 | 92.0 | 92.3 | 91.5 | 92.4 | 90.2 |
| Plasma etching rate (%) | | 6.1 | 6.2 | 6.8 | 6.1 | 6.2 | 6.2 | 7.1 | 7.8 |
| Light transmittance (%. @405 nm) | | 7.2 | 7.9 | 7.6 | 2.1 | 9.7 | 99 | 99 | 21 |

As shown in Table 1, the encapsulation compositions according to the present invention had low light transmittances at a wavelength of 420 nm or less, low plasma etching rates, and high photocuring rates. Conversely, the encapsulation compositions of Comparative Examples 1 and 2 prepared without the indole based photocurable monomer according to the present invention had high light transmittance at a wavelength of 420 nm or less, and the encapsulation composition of Comparative Example 2 had a high plasma etching rate.

In addition, the encapsulation composition of Comparative Example 3 prepared using an UV absorbent containing an indole based functional group substantially similar to the indole based photocurable monomer according to the present invention could not be used over an amount of 1% due to a solubility problem and had problems of a high light transmittance at 420 nm or less and a high plasma etching rate when present in an amount of 1%.

It should be understood that various modifications, changes, alterations, and equivalent embodiments can be made by those skilled in the art without departing from the spirit and scope of the present invention.

The invention claimed is:

1. A composition for encapsulating an organic light emitting diode, comprising: an indole based photocurable monomer; a non-indole based photocurable monomer; and an initiator, wherein the indole based photocurable monomer is represented by Formula 1:

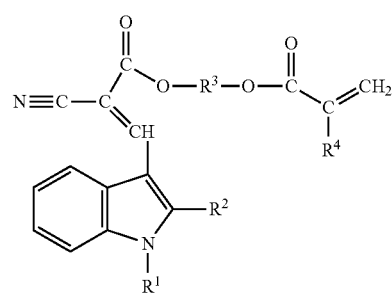

<Formula 1> in Formula 1, $R^1$ is a substituted or unsubstituted $C_1$ to $C_{10}$ alkyl group, a substituted or unsubstituted $C_6$ to $C_{20}$ aryl group, or a substituted or unsubstituted $C_7$ to $C_{20}$ arylalkyl group, $R^2$ is a substituted or unsubstituted $C_6$ to $C_{20}$ aryl group, $R^3$ is a substituted or unsubstituted $C_1$ to $C_{10}$ alkylene group or a substituted or unsubstituted $C_1$ to $C_{10}$ alkyleneoxy group, and $R^4$ is a hydrogen atom or a substituted or unsubstituted $C_1$ to $C_5$ alkyl group.

2. A composition for encapsulating an organic light emitting diode, comprising: an indole based photocurable monomer; a non-indole based photocurable monomer; and an initiator, wherein the indole based photocurable monomer is represented by at least one of Formula 1-1 to Formula 1-4:

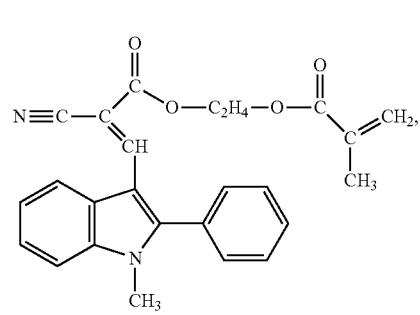

<Formula 1-1>

<Formula 1-2>

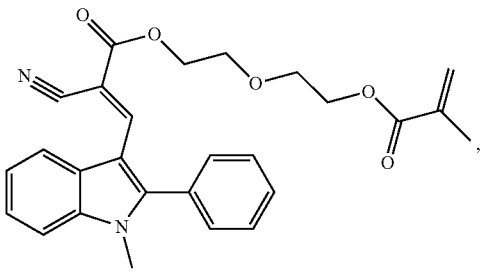

<Formula 1-3>

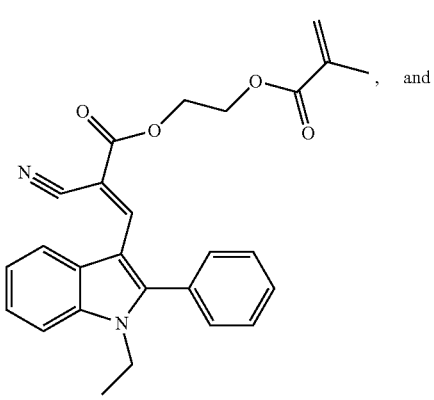
, and

<Formula 1-4>

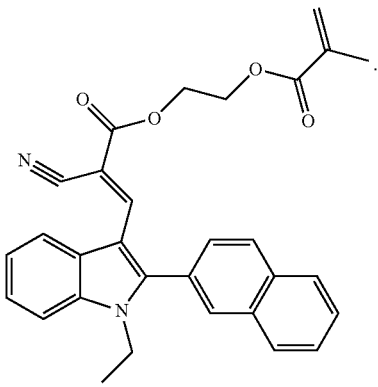

3. The composition for encapsulating an organic light emitting diode according to claim 1, wherein the indole based photocurable monomer is present in an amount of 1 wt % to 10 wt % based on the total amount of the indole based photocurable monomer, the non-indole based photocurable monomer, and the initiator.

4. The composition for encapsulating an organic light emitting diode according to claim 1, wherein the non-indole based photocurable monomer comprises a mixture of a monofunctional monomer and a polyfunctional monomer.

5. The composition for encapsulating an organic light emitting diode according to claim 4, wherein the monofunctional monomer comprises (B1) an aromatic mono(meth)acrylate alone or a mixture of the (B1) aromatic mono(meth)acrylate and (B2) a non-aromatic mono(meth)acrylate.

6. The composition for encapsulating an organic light emitting diode according to claim 5, wherein the aromatic mono(meth)acrylate (B1) is represented by Formula 2:

<Formula 2>

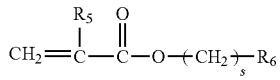

in Formula 2,
R$^5$ is a hydrogen atom or a methyl group, s is an integer of 0 to 10, and R$_6$ is a substituted or unsubstituted C$_6$ to C$_{50}$ aryl group or a substituted or unsubstituted C$_6$ to C$_{50}$ aryloxy group.

7. The composition for encapsulating an organic light emitting diode according to claim 4, wherein the polyfunctional monomer comprises a non-silicone based di(meth)acrylate (C1) alone or a mixture of the non-silicone based di(meth)acrylate (C1) and a silicone based di(meth)acrylate (C2).

8. The composition for encapsulating an organic light emitting diode according to claim 7, wherein the silicone based di(meth)acrylate (C2) is represented by Formula 4:

<Formula 4>

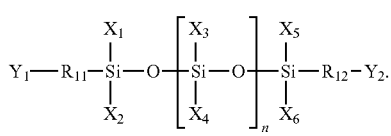

in Formula 4,
R$_{11}$ and R$_{12}$ are identical to or different from each other, and R$_{11}$ and R$_{12}$ are independently a single bond; a substituted or unsubstituted C$_1$ to C$_{20}$ alkylene group; a substituted or unsubstituted C$_1$ to C$_{30}$ alkylene ether group; *—N(R')—R"—*, wherein * is a linking site of an element, R' is a substituted or unsubstituted C$_1$ to C$_{30}$ alkyl group, and R" is a substituted or unsubstituted C$_1$ to C$_{20}$ alkylene group: a substituted or unsubstituted C$_6$ to C$_{30}$ arylene group; a substituted or unsubstituted C$_7$ to C$_{30}$ arylalkylene group; or *—O—R"—*"—*, wherein * is a linking site of an element, and R" is a substituted or unsubstituted C$_1$ to C$_{20}$ alkylene group,
X$_1$, X$_2$, X$_3$, X$_4$, X$_5$, and X$_6$ are identical to or different from each other, and X$_1$, X$_2$, X$_3$, X$_4$, X$_5$, and X$_6$ are independently a hydrogen atom or a substituted or unsubstituted C$_1$ to C$_{30}$ alkyl group, a substituted or unsubstituted C$_1$ to C$_{30}$ alkyl ether group, *—N(R')(R"), a substituted or unsubstituted C$_1$ to C$_{30}$ alkylsulfide group, a substituted or unsubstituted C$_6$ to C$_{30}$ aryl group, or a substituted or unsubstituted C$_7$ to C$_{30}$ arylalkyl group, and at least one of X$_1$, X$_2$, X$_3$, X$_4$, X$_5$ and X$_6$ is a substituted or unsubstituted C$_6$ to C$_{30}$ aryl group,
Y$_1$ and Y$_2$ are identical to or different from each other, and Y$_1$ and Y$_2$ are independently represented by Formula 5:

<Formula 5>

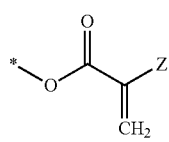

in Formula 5,
* is a linking site of an element, and Z is a hydrogen atom or a substituted or unsubstituted $C_1$ and $C_{30}$ alkyl group.

9. The composition for encapsulating an organic light emitting diode according to claim 1, comprising:
   1 wt % to 10 wt % of the indole based photocurable monomer;
   50 wt % to 98 wt % of the non-indole based photocurable monomer; and
   1 wt % to 40 wt % of the initiator.

10. An organic light emitting diode display, comprising:
    an organic light emitting diode; and
    a barrier stack formed on the organic light emitting diode and comprising an inorganic barrier layer and an organic barrier layer,
    wherein the organic barrier layer is formed of the composition for encapsulating an organic light emitting diode according to claim 3.

11. The composition for encapsulating an organic light emitting diode according to claim 2, wherein the indole based photocurable monomer is present in an amount of 1 wt % to 10 wt % based on the total amount of the indole based photocurable monomer, the non-indole based photocurable monomer, and the initiator.

12. The composition for encapsulating an organic light emitting diode according to claim 2, wherein the non-indole based photocurable monomer comprises a mixture of a monofunctional monomer and a polyfunctional monomer.

13. The composition for encapsulating an organic light emitting diode according to claim 12, wherein the monofunctional monomer comprises (B1) an aromatic mono(meth)acrylate alone or a mixture of the (B1) aromatic mono(meth)acrylate and (B2) a non-aromatic mono(meth)acrylate.

14. The composition for encapsulating an organic light emitting diode according to claim 13, wherein the aromatic mono(meth)acrylate (B1) is represented by Formula 2:

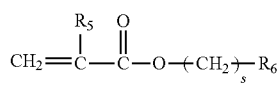

<Formula 2> in Formula 2,
$R_5$ is a hydrogen atom or a methyl group, s is an integer of 0 to 10, and $R_6$ is a substituted or unsubstituted $C_6$ to $C_{50}$ aryl group or a substituted or unsubstituted $C_6$ to $C_{50}$ aryloxy group.

15. The composition for encapsulating an organic light emitting diode according to claim 12, wherein the polyfunctional monomer comprises a non-silicone based di(meth)acrylate (C1) alone or a mixture of the non-silicone based di(meth)acrylate (C1) and a silicone based di(meth)acrylate (C2).

16. The composition for encapsulating an organic light emitting diode according to claim 15, wherein the silicone based di(meth)acrylate (C2) is represented by Formula 4:

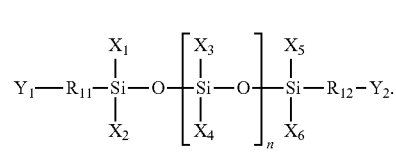

<Formula 4> in Formula 4,
$R_{11}$ and $R_{12}$ are identical to or different from each other, and $R_{11}$ and $R_{12}$ are independently a single bond; a substituted or unsubstituted $C_1$ to $C_{20}$ alkylene group; a substituted or unsubstituted $C_1$ to $C_{30}$ alkylene ether group; *—N(R')—R"—*, wherein * is a linking site of an element, R' is a substituted or unsubstituted $C_1$ to $C_{30}$ alkyl group, and R" is a substituted or unsubstituted $C_1$ to $C_{20}$ alkylene group; a substituted or unsubstituted $C_6$ to $C_{30}$ arylene group; a substituted or unsubstituted $C_7$ to $C_{30}$ arylalkylene group; or *—O—R"—*"—*, wherein * is a linking site of an element, and R" is a substituted or unsubstituted $C_1$ to $C_{20}$ alkylene group, $X_1$, $X_2$, $X_3$, $X_4$, $X_5$, and $X_6$ are identical to or different from each other, and $X_1$, $X_2$, $X_3$, $X_4$, $X_5$, and $X_6$ are independently a hydrogen atom or a substituted or unsubstituted $C_1$ to $C_{30}$ alkyl group, a substituted or unsubstituted $C_1$ to $C_{30}$ alkyl ether group, *—N(R')(R"), a substituted or unsubstituted $C_1$ to $C_{30}$ alkylsulfide group, a substituted or unsubstituted $C_6$ to $C_{30}$ aryl group, or a substituted or unsubstituted $C_7$ to $C_{30}$ arylalkyl group, and at least one of $X_1$, $X_2$, $X_3$, $X_4$, $X_5$ and $X_6$ is a substituted or unsubstituted $C_6$ to $C_{30}$ aryl group, $Y_1$ and $Y_2$ are identical to or different from each other, and $Y_1$ and $Y_2$ are independently represented by Formula 5:

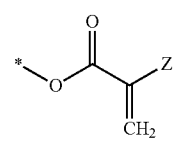

<Formula 5> in Formula 5,
* is a linking site of an element, and Z is a hydrogen atom or a substituted or unsubstituted $C_1$ to $C_{30}$ alkyl group.

17. The composition for encapsulating an organic light emitting diode according to claim 2, comprising:
    1 wt % to 10 wt % of the indole based photocurable monomer;
    50 wt % to 98 wt % of the non-indole based photocurable monomer; and
    1 wt % to 40 wt % of the initiator.

18. An organic light emitting diode display, comprising:
    an organic light emitting diode; and
    a barrier stack formed on the organic light emitting diode and comprising an inorganic barrier layer and an organic barrier layer,
    wherein the organic barrier layer is formed of the composition for encapsulating an organic light emitting diode according to claim 4.

* * * * *